United States Patent [19]

Anderson et al.

[11] Patent Number: 4,745,113

[45] Date of Patent: May 17, 1988

[54] PESTICIDAL BENZOYLUREA COMPOUNDS, COMPOSITIONS AND USE

[75] Inventors: Martin Anderson; Anthony G. Brinnand, both of Kent, England

[73] Assignee: E. I. Du Pont de Nemours and Company, Wilmington, Del.

[21] Appl. No.: 906,361

[22] Filed: Sep. 10, 1986

[30] Foreign Application Priority Data

Sep. 25, 1985 [GB] United Kingdom ............... 8523606

[51] Int. Cl.⁴ .............. A01N 43/84; A01N 43/60; C07D 265/32; C07D 279/12
[52] U.S. Cl. .............. 514/226.8; 514/227.5; 514/228.8; 514/238.2; 514/255; 514/327; 514/425; 544/58.2; 544/159; 544/383; 546/216; 548/542; 560/16
[58] Field of Search .............. 544/159, 58.2, 383; 546/216, 231; 548/542; 514/222, 229, 255, 327, 425

[56] References Cited

U.S. PATENT DOCUMENTS 4,623,658 11/1986 Anderson ..................... 548/542

Primary Examiner—Robert W. Ramsuer

[57] ABSTRACT

Compounds of the general formula

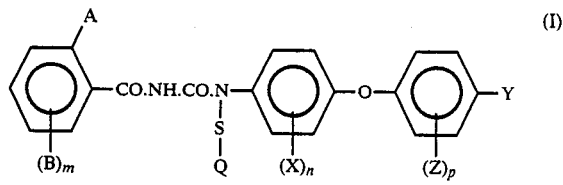

in which each of A and B independently represents a halogen atom or an alkyl group; m is 0 or 1; Q represents a group of general formula

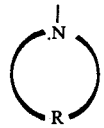

in which R is as defined, or Q represents a group of general formula $-CR^2R^3R_4$ in which $R^2$, $R^3$ and $R^4$ are as defined; together with processes for the preparation of such compounds, pesticidal compositions containing them and their pesticidal use, and certain novel intermediates.

9 Claims, No Drawings

PESTICIDAL BENZOYLUREA COMPOUNDS, COMPOSITIONS AND USE

The present invention relates to benzoylurea compounds having pesticidal, especially insecticidal and acaricidal, activity.

The invention provides a compound of the general formula

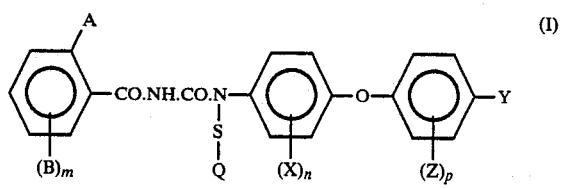

in which each of A and B independently represents a halogen atom or an alkyl group; m is 0 or 1; Q represents a group of general formula

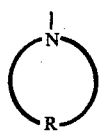

in which R represents an optionally substituted alkylene group in which a —CH$_2$— group is replaced by an oxygen or sulphur atom or by a sulphone or sulphoxide group, or by a group N—R$^1$ in which R$^1$ represents an optionally substituted alkyl, alkylcarbonyl, alkoxycarbonyl, dialkylaminocarbonyl, alkylsulphonyl or arylsulphonyl group, and/or in which a —CH$_2$— group is replaced by a carbonyl or thiocarbonyl group, or Q represents a group of general formula —CR$^2$R$^3$R$^4$ in which R$^2$ represents a hydrogen atom or an optionally substituted alkyl group, R$^3$ represents a halogen atom or a cyano or nitro group, or an optionally substituted alkylcarbonyl, alkoxycarbonyl, arylcarbonyl, aryloxycarbonyl or dialkylaminocarbonyl group, and R$^4$ represents any one of the moieties specified for R$^2$ and/or R$^3$, or R$^2$ and R$^4$ together represent an optionally substituted alkylene group, or R$^3$ and R$^4$ together represent a group of general formula

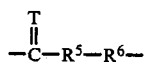

in which T represents a sulphur or oxygen atom, R$^5$ represents an optionally substituted alkylene group and R$^6$ represents a methylene, carbonyl or thiocarbonyl group; the optional substituents for an alkyl moiety or alkylene group being selected from halogen atoms and cyano, alkoxy, haloalkoxy, alkylcarbonyl, haloalkylcarbonyl, alkoxycarbonyl and haloalkoxycarbonyl groups and the optional substituents for an aryl group being selected from these substituents and also from alkyl, haloalkyl and nitro groups; X represents a halogen atom or a cyano, nitro, alkyl or haloalkyl group; each of Y and Z independently represents a halogen atom or a cyano, nitro or haloalkyl group; n is 0, 1, 2, 3 or 4; and p is 0, 1 or 2.

Except where otherwise stated, throughout this Specification and claims, any alkyl moiety preferably has up to 6, especially up to 4, carbon atoms. Halogen atoms may be fluorine, chlorine, bromine or iodine atoms, with fluorine and chlorine being preferred. When n or p is greater than 1, the substituents X or Z present may be the same or different.

R preferably has 3 to 8 atoms in the chain, 4 or 5 being most preferred. R$^5$ preferably has 1 to 6 atoms in the chain. Preferably each of A and B independently represents a fluorine or chlorine atom or a methyl group. Most preferably, A is a fluorine atom, m is 1 and B is a fluorine or chlorine atom, preferably in the 6-position of the phenyl ring (A of course being in the 2-position).

Preferably X represents a fluorine or chlorine atom or a methyl group. Thus (X)$_n$ could be 4 fluorine atoms, 3 fluorine atoms and a chlorine atom, or two fluorine atoms and two chlorine atoms. Most preferably X represents fluorine and n is 4, 3, 2, 1, or 0. In especially preferred embodiments n is 1 and X is a fluorine atom ortho to the nitrogen atom.

Preferably Y represents a chlorine atom or a nitro, cyano or trifluoromethyl group. A trifluoromethyl group Y is especially preferred.

Preferably Z represents a chlorine atom or a cyano or nitro group. Preferably p is 0 or 1. Most preferably Z represents a chlorine atom and p is 1; such a chlorine atom is preferably in the position ortho to the oxygen linkage.

It is preferred that Q represents a group of general formula

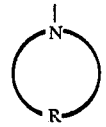

in which R represents an optionally substituted alkylene group in which a —CH$_2$— group is replaced by an oxygen atom and/or in which a —CH$_2$— group is replaced by a carbonyl group, or Q represents a group of general formula —CR$^2$R$^3$R$^4$ in which R$^2$ represents a hydrogen atom or an optionally substituted alkyl group, R$^3$ represents a halogen atom or a cyano, nitro, optionally substituted alkylcarbonyl, alkoxycarbonyl or dialkylaminocarbonyl group, and R$^4$ represents any one of the moieties specified for R$^2$ and/or R$^3$, or R$^3$ and R$^4$ together represent a group of general formula

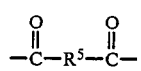

in which R$^5$ represents an optionally substituted alkylene group.

When Q represents a group of general formula —CR$^2$R$^3$R$^4$, it is preferred that R$^2$ represents an alkyl, especially methyl, group, R$^3$ represents an alkylcarbonyl or alkoxycarbonyl group, and R$^4$ represents an alkyl, alkylcarbonyl or alkoxycarbonyl group. Particularly preferred compounds are those wherein R$^2$ represents a methyl group; R$^3$ represents a methylcarbonyl, propylcarbonyl or ethoxycarbonyl group; and R$^4$ represents an ethoxycarbonyl or methyl group.

Examples of Q representing a group of general formula

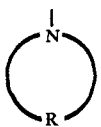

are N-morpholinyl, N-piperidonyl, N-pyrrolidonyl and N-morpholinonyl.

The invention also provides a process for the preparation of a compound of the general formula I, which comprises reacting a compound of the general formula

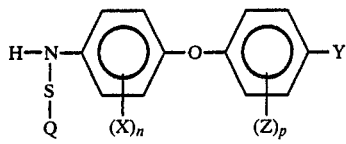

(II)

with a compound of the general formula

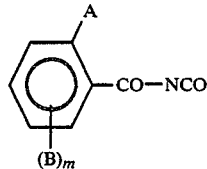

(III)

in which A, B, m, X, Y, Z, Q, n and p have the meanings given for the general formula I.

The reaction is suitably carried out in the presence of a solvent. Suitable solvents are aromatic solvents such as benzene, toluene, xylene, or chlorobenzene, hydrocarbons such as petroleum fractions, chlorinated hydrocarbons such as chloroform, methylene chloride or dichloroethane, and ethers such as diethyl ether, dibutyl ether, or dioxan. Mixtures of solvents are also suitable.

Preferably the reaction is carried out at a temperature from 0° C. to 100° C., suitably ambient temperature. Preferably the molar ratio of isocyanate to amine is from 1:1 to 2:1. Preferably the reaction is carried out under anhydrous conditions.

The compounds of formula II are themselves novel and constitute a further aspect of the invention; they may be prepared by reacting a compound of the general formula

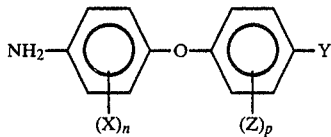

(IV)

with a compound of the general formula

 Hal—S—Q (V)

in which Hal represents a halogen atom.

The reaction between the compounds of formulae IV and V is preferably carried out in the presence of an inert solvent, for example a hydrocarbon or chlorinated hydrocarbon, and the reaction temperature is preferably in the range of from 0° to 100° C., preferably 10° to 30° C. The reaction is suitably carried out in the presence of an inorganic or organic base. Preferably an amine such as triethylamine is used.

The compounds of formula IV may be prepared by reacting a compound of general formula

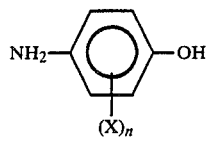

(VI)

with a compound of the general formula

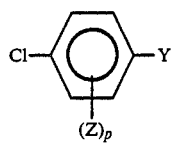

(VII)

in which X, n, Y, Z, and p have the meanings given for the compound of general formula IV.

The reaction between the compounds of formulae VI and VII is preferably carried out in the presence of an inert solvent, for example a polar aprotic solvent such as dimethylsulphoxide or dimethylformamide, in the presence of a base, for example an alkali metal hydroxide, alkoxide or carbonate, or an organic base. The reaction temperature is suitably in the range of from 0° to 150° C., preferably 30° to 100° C.

Certain compounds of the general formula V are novel and constitute a further aspect of the invention. In this aspect the invention provides compounds of the general formula V in which Q represents a group of general formula —$CR^2R^3R^4$ in which $R^2$ represents a hydrogen atom or an optionally substituted alkyl group, and $R^3$ and $R^4$ each independently represents a cyano or nitro group, or an optionally substituted alkylcarbonyl, alkoxycarbonyl, arylcarbonyl, aryloxycarbonyl or dialkylaminocarbonyl group.

The compounds of general formula V may be prepared by reacting a sulphenyl halide compound of general formula $S(Hal)_2$ with a compound of general formula Q—H. The reaction is preferably carried out in the presence of an inert solvent, for example a hydrocarbon or halogenated hydrocarbon, and may be carried out at a temperature from −10° to 100° C.

The compounds of the general formula I exhibit pesticidal, for example insecticidal and acaricidal, activity. Accordingly the invention also provides a pesticidal composition comprising a compound of the general formula I together with a carrier. The invention further provides a method of combating pests at a locus, which comprises applying to the locus a pesticidal compound or composition according to the invention.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing pesticidal, herbicidal, or fungicidal properties. The compounds of the invention are especially useful when applied in admixture with other insecticides, especially organophosphates and pyrethroids. Mixtures with the commercial products fenvalerate, permethrin, cypermethrin, deltamethrin and alphamethrin are especially useful.

The following Examples illustrate the invention. Example 1 illustrates the preparation of the intermediate of the general formula IV. Examples 2 and 5 illustrate the preparation of intermediates of the general formula V, and Examples 3 and 6, intermediates of the general formula II. Examples 4 and 7 to 11 illustrate the preparation of compounds of the general formula I.

EXAMPLE 1

Preparation of 2-fluoro-4-[2-chloro-4-(trifluoromethyl)phenoxy]aniline

A solution of 2-fluoro-4-hydroxyaniline (7.1 g) and potassium hydroxide (3.7 g, 85% pure) in dimethylsulphoxide (25 ml) was heated to 80° C. and treated with a solution of 1,2-dichloro-4-(trifluoromethyl)benzene (10.9 g) in dimethylsulphoxide (10 ml). The mixture was stirred at 90°–95° C. for 20 hours, after which time it was diluted with a mixture of water and dichloromethane. The organic phase was dried over sodium sulphate and evaporated down to give 3.6 g of the crude desired product as a brown oil.

Chromatography over silica gel using toluene/petroleum ether (4:1 ratio) gave 1.1 g of the pure amine as a yellow oil.

EXAMPLE 2

Preparation of (alpha-methyl-alpha-chlorosulphenyl)diethylmalonate

Sulphur dichloride (11.3 g) in 1,2 dichloroethane (20 ml) was added to diethyl methyl malonate (17.4 g) in 1,2-dichloroethane, over 10 minutes, at ambient temperature. The solution was refluxed for 8 hours. Distillation yielded the title compound. (15.6 g), b.p. 120°-3° C./12 mmHg.

EXAMPLE 3

Preparation of diethyl 4-[4-[2-chloro-4-(trifluoromethyl)phenoxy]-2-fluorophenyl]-3-thia-4-azabutane-2,2-dicarboxylate A solution of the compound prepared in Example 2 (5.3 g), in diethyl ether (10 ml), was added over 30 minutes to a solution of triethylamine (2.2 g) and the compound prepared in Example 1 (6.1 g), in diethyl ether (50 ml). The solution was stirred at ambient temperature for 6 hours. Diethyl ether (150 ml) was added, the solution was washed with water and dried, and the diethyl ether was removed by evaporation. Column chromatography on silica using dichloromethane as eluant yielded 8 g of the title compound as a clear, colourless oil.

EXAMPLE 4

Preparation of diethyl 4-[4-[2-chloro-4-(trifluoromethyl)phenoxy]-2-fluorophenyl]-7-(2,6-difluorophenyl)-5,7-dioxo-3-thia-4,6-diazaheptane-2,2-dicarboxylate 2,6-Difluorobenzoylisocyanate (3 g) in a 1:1 (v/v) mixture of toluene and petroleum ether (10 ml) was added to a solution of the compound produced by Example 3 (7.6 g) in the same solvent (15 ml), over 30 minutes at 15°-20° C. The solution was stirred for 6 hours at ambient temperature and the solvent was removed by evaporation. Column chromatography on silica using a 1:1 (v/v) mixture of diethyl ether and petroleum ether yielded the title compound as a gum (9.5 g).

| Analysis | C | H | N |
| --- | --- | --- | --- |
| Calculated (%) | 50.3 | 3.3 | 4.0 |
| Found (%) | 50.5 | 3.6 | 4.1 |

EXAMPLE 5

Preparation of (4-morpholinyl)sulphenyl chloride

Pyridine (8.7 g) dissolved in dichloromethane (25 ml) was added, over 20 minutes at 5°-10° C., to a solution of sulphur dichloride (11.3 g) in dichloromethane (25 ml). A solution of morpholine (8.7 g) in dichloromethane (25 ml) was added, over 20 minutes at 5°-10° C. The solution was stirred for four hours and the temperature allowed to rise to ambient temperature. The solution was filtered and the solvent was evaporated off. Diethyl ether was added, the resulting suspension was filtered and the filtrate evaporated. Distillation of the residue yielded the title compound (8.2 g), b.p. 60° C./0.5 mmHg.

EXAMPLE 6

Preparation of [4-[2-chloro-4-(trifluoromethyl)phenoxy]-2-fluorophenyl][(4-morpholinyl)thio]amine The compound prepared in Example 5 (3.4 g) was dissolved in diethyl ether (10 ml). The solution was added to a solution of triethylamine (2.2 g) and the compound prepared in Example 1 (6.1 g) in diethyl ether (50 ml) at 15°-20° C. The solution was stirred for 20 minutes, diethyl ether was added (20 ml), the solution was washed with water, and dried. The solvent was removed by evaporation. Column chromatography on silica using 50:50 (v/v) diethyl ether-dichloromethane as eluant yielded the title compound as a brown oil (5 g).

EXAMPLE 7

Preparation of N-[[[4-[2-chloro-4-(trifluoromethyl)phenoxy]-2-fluorophenyl][(4-morpholinyl)thio]amino]carbonyl]-2,6-difluorobenzamide 2,6-Difluorobenzoyl isocyanate (1.4 g) in a 1:1 (v/v) mixture of toluene and petroleum ether (10 ml) was added to a solution of the compound produced by Example 6 (3 g) in the same solvent (15 ml), at ambient temperature. The solution was stirred for two hours and placed in a freezer overnight (−5° to 0° C.). The solvent was removed by evaporation, and the residue was chromatographed twice on silica, firstly using dichloromethane as eluant and secondly using a 1:1 (v/v) mixture of diethyl ether and petroleum ether, to yield the title compound (2.5 g), m.p. 77°-80° C.

| Analysis | C | H | N |
| --- | --- | --- | --- |
| Calculated (%) | 49.5 | 3.0 | 6.9 |
| Found (%) | 50.1 | 3.4 | 6.7 |

EXAMPLE 8

N-[[[4-[2-chloro-4-(trifluoromethyl)phenoxy]-2-fluorophenyl][(2-oxo-1-pyrrolidinyl)thio]amino]carbonyl]-2,6-difluorobenzamide The title compound was prepared in a similar manner to the compounds of Examples 4 and 7, m.p. 166°-8° C.

| Analysis | C | H | N |
| --- | --- | --- | --- |
| Calculated (%) | 49.7 | 2.7 | 7.0 |
| Found (%) | 49.6 | 2.7 | 7.2 |

Freshly prepared (2-oxo-1-pyrrolidinyl)-sulphenyl chloride, a dark red oil, was used without further purification to prepare the further intermediate [4-[2-chloro-4-(trifluoromethyl)phenoxy]-2-fluorophenyl][(2-oxo-1-pyrrolidinyl)thio]amine, which was a crystalline compound, (mp 125°-126° C.).

EXAMPLE 9

N-[[[4-[2-chloro-4-(trifluoromethyl)phenoxy]-2-fluorophenyl][(2-oxo-1-piperidinyl)thio]amino]carbonyl]-2,6-difluorobenzamide The title compound was prepared in a similar manner to the compounds of Examples 4 and 7, m.p. 139°–141° C.

| Analysis | C | H | N |
|---|---|---|---|
| Calculated (%) | 50.5 | 2.9 | 6.8 |
| Found (%) | 50.6 | 3.0 | 6.9 |

Freshly prepared (2-oxo-1-piperidinyl)-sulphenyl chloride was used, without further purification, in the preparation of [4-[2-chloro-4-(trifluoromethyl)phenoxy]-2-fluorophenyl][2-oxo-1-piperidinyl)thio]amine, which was a crystalline compound (mp 128°–130° C.).

EXAMPLES 10 AND 11

Following procedures similar to those described in Examples 1–4, but substituting the diethyl methyl malonate (Example 2) with (10)ethyl-2-methyl acetoacetate, or (11) diisopropyl ketone, there were obtained, respectively, compounds of the formula:

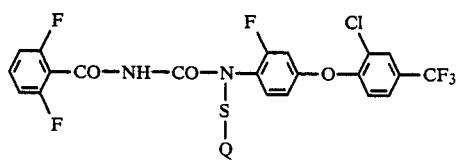

wherein Q has the structure:

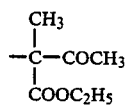 (Ex. 10)

or

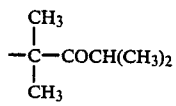 (Ex. 11)

The compound of Example 10 was a pale brown oil,
Analysis Calc.: C 50.7; H 3.2; N 4.2. Found: C 50.3; H 3.7; N 3.9.

The compound of Example 11 was a white solid, m.pt. 148°–150° C.
Analysis Calc.: C 53.1; H 3.6; N 4.4. Found: C 53.3; H 3.7; N 4.8.

EXAMPLE 12

Insecticidal Activity

The insecticidal activity of the compounds of the invention was determined in the following tests, employing the insects *Spodoptera littoralis* (S.l.) and *Aedes aegypti* (A.a)

The test methods used for each species appear below. In each case the tests were conducted under normal conditions (23° C.±2° C.; fluctuating light and humidity).

In each test an $LC_{50}$ (the dosage of active material required to kill half of the test species) for the compound was calculated from the mortality figures and compared with the corresponding $LC_{50}$ for a standard insecticide, ethyl parathion, in the same tests. The results are expressed as toxicity indices thus:

$$\text{toxicity index} = \frac{LC_{50}(\text{parathion})}{LC_{50}(\text{test compound})} \times 100$$

and are set out in Table I below.

(i) *Spodoptera Littoralis* (S.l.)

Solutions or suspensions of the compound were made up over a range of concentrations in 10% acetone/water containing 0.025% Triton X100 ("Triton" is a registered trade mark). These solutions were sprayed using a logarithmic spraying machine onto petri dishes containing a nutritious diet on which the *Spodoptera littoralis* larvae had been reared. When the spray deposit had dried each dish was infested with 10 2nd instar larvae. Mortality assessments were made 7 days after spraying.

(ii) *Aedes aegypti* (A.a.)

Several solutions of the test compound of varying concentration were prepared in acetone. 100 microliter quantities were added to 100 ml of tap water, the acetone being allowed to evaporate off. 10 early 4th instar larvae were placed in the test solution; after 48 hours the (surviving) larvae were fed with animal feed pellets, and the final percentage mortality assessed when all the larvae had either pupated and emerged as adults or died.

The results are given in Table I.

TABLE I

| | Insecticidal Activity | |
|---|---|---|
| | Toxicity Index | |
| Compound of Example No. | S.l. | A.a. |
| 4 | 4200 | 1400 |
| 7 | 4500 | 290 |
| 8 | 2800 | 2100 |
| 9 | 3800 | 680 |
| 10 | 9500 | 540 |
| 11 | 4400 | 120 |

EXAMPLE 13

Acaricidal Activity

Leaf discs were infested with 30–60 larvae of the mite *Tetranicus urticae* and sprayed with varying dosages of solutions of the test compound made up as in test (i) of Example 12 above. When dry, the discs were maintained at constant temperature for 12 days, after which mortality assessments were made, and the $LC_{50}$ values calculated, that is, the dosage of active material required to kill half of the test species. The results are given in table II below.

TABLE II

| | Acaricidal Activity |
|---|---|
| Compound of Example No. | $LC_{50}$ (% active ingredient in spray) |
| 4 | 0.00049 |
| 7 | 0.00015 |
| 8 | 0.00037 |
| 9 | 0.00024 |
| 10 | 0.00017 |
| 11 | 0.00013 |

We claim:
1. A compound of the general formula

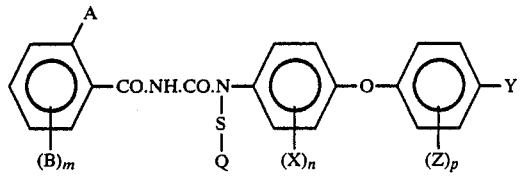 (I)

in which each of A and B independently represents a halogen atom or an alkyl group; m is 0 or 1; Q represents a group of general formula

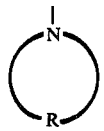

in which R represents an optionally substituted alkylene group in which a —CH$_2$— group is replaced by an oxygen or sulphur atom or by a sulphone or sulphoxide group, or by a group N—R$^1$ in which R$^1$ represents an optionally substituted alkyl, alkylcarbonyl, alkoxycarbonyl, dialkylaminocarbonyl, alkylsulphonyl or arylsulfonyl group, and in which a —CH$_2$— group is replaced by a carbonyl or thiocarbonyl group; the optional substituents for an alkyl moiety or alkylene group being selected from halogen atoms and cyano, alkoxy, haloalkoxy, alkylcarbonyl, haloalkylcarbonyl, alkoxycarbonyl and haloalkoxycarbonyl groups and the optional substituents for an aryl group being selected from these substituents and also from alkyl, haloalkyl and nitro groups; X represents a halogen atom or a cyano, nitro, alkyl or haloalkyl group; each of Y and Z independently represents a halogen atom or a cyano, nitro or haloalkyl group; n is 0, 1, 2, 3 or 4; and p is 0, 1 or 2.

2. An acaricidal or insecticidal composition comprising an acaricidally or insecticidally effective amount of a compound according to claim 1 together with a carrier.

3. A composition according to claim 2 in admixture with an insecticidally effective amount of an organophosphate or pyrethroid.

4. A method for combatting an acaricidal pest comprising applying to the locus of the pest an acaricidally effective amount of a compound according to claim 1.

5. A method for combatting an acaricidal pest comprising applying to the locus of the pest an acaricidally effective amount of a composition according to claim 2.

6. A method for combatting an acaricidal pest comprising applying to the locus of the pest an acaricidally effective amount of a composition according to claim 3.

7. A method for combatting an insecticidal pest comprising applying to the locus of the pest an insecticidally effective amount of a compound according to claim 1.

8. A method for combatting an insecticidal pest comprising applying to the locus of the pest an insecticidally effective amount of a composition according to claim 2.

9. A method for combatting an insecticidal pest comprising applying to the locus of the pest an insecticidally effective amount of a composition according to claim 3.

* * * * *